United States Patent [19]

Kunz et al.

[11] Patent Number: 5,051,436
[45] Date of Patent: Sep. 24, 1991

[54] COMPOSITIONS FOR PROTECTING PLANTS AGAINST DISEASE

[75] Inventors: Walter Kunz, Oberwil; Rolf Schurter, Binningen, both of Switzerland

[73] Assignee: Ciba-Geigy Corporation, Ardsley, N.Y.

[21] Appl. No.: 481,422

[22] Filed: Feb. 16, 1990

[30] Foreign Application Priority Data

Feb. 21, 1989 [CH] Switzerland ............... 617/89

[51] Int. Cl.$^5$ ............... C07D 285/14; C07D 417/06; A01N 43/82
[52] U.S. Cl. ............... 514/361; 514/212; 514/322; 514/338; 540/524; 546/199; 546/261; 548/126
[58] Field of Search ............... 548/126; 546/199, 261; 540/524; 514/361, 212, 322, 338

[56] References Cited

U.S. PATENT DOCUMENTS 4,931,581 6/1990 Schurter ............... 560/18

FOREIGN PATENT DOCUMENTS 1176799 1/1970 United Kingdom .

Primary Examiner—Robert Gerstl
Attorney, Agent, or Firm—George R. Dohmann; Edward McC. Roberts

[57] ABSTRACT

Novel N-acyl- and N-sulfonylbenzo-1,2,3-thiadiazole-7-carboxylic acid amides of formula

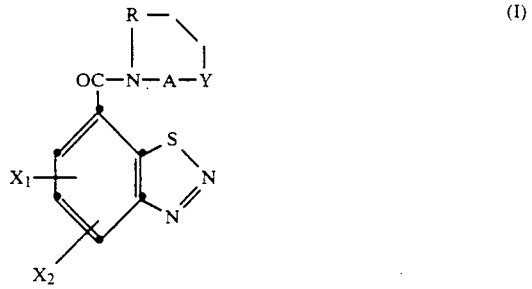

in which $X_1$ and $X_2$ independently of one another are each hydrogen or together 1 to 3 halogen atoms; A is sulfonyl or carbonyl; Y is phenyl or phenyl substituted by $C_1$-$C_2$alkyl, $C_1$-$C_2$alkoxy, halogen, $C_1$-$C_2$haloalkyl, $C_1$-$C_2$alkoxycarbonyl, $C_1$-$C_3$alkanoyloxymethyl, cyano and/or by nitro; R is hydrogen, $C_1$-$C_4$alkyl, $C_1$-$C_4$haloalkyl, $C_3$-$C_5$alkenyl or $C_3$-$C_5$alkynyl; and in which, furthermore, the group

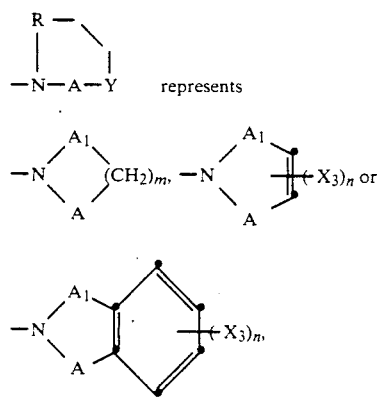

wherein $A_1$ is methylene, carbonyl or sulfonyl; $X_3$ is hydrogen, methyl or halogen; m is 2, 3 or 4; and n is zero, 1 or 2.

The novel active ingredients have plant-protecting properties and are suitable especially for the preventive protection of plants against attack by phytopathogenic microorganisms such as fungi, bacteria and viruses.

13 Claims, No Drawings

COMPOSITIONS FOR PROTECTING PLANTS AGAINST DISEASE

The present invention relates to novel N-acyl- and N-sulfonylbenzo-1,2,3-thiadiazole-7-carboxylic acid amides of the following formula I. The invention relates also to the preparation of those substances and to compositions containing at least one of those compounds as active ingredient. The invention furthermore relates to the preparation of the said compositions and to the use of the active ingredients or compositions for protecting plants against attack by harmful microorganisms, for example plant-damaging fungi, bacteria and viruses.

The compounds of the invention correspond to the general formula I

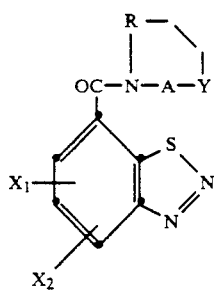
(I)

in which $X_1$ and $X_2$ independently of one another are each hydrogen or together 1 to 3 halogen atoms; A is sulfonyl or carbonyl; Y is phenyl or phenyl substituted by $C_1$-$C_2$alkyl, $C_1$-$C_2$alkoxy, halogen, $C_1$-$C_2$haloalkyl, $C_1$-$C_2$alkoxycarbonyl, $C_1$-$C_3$alkanoyloxymethyl, cyano and/or by nitro; R is hydrogen, $C_1$-$C_4$alkyl, $C_1$-$C_4$haloalkyl, $C_3$-$C_5$alkenyl or $C_3$-$C_5$alkynyl; and in which, furthermore, the group

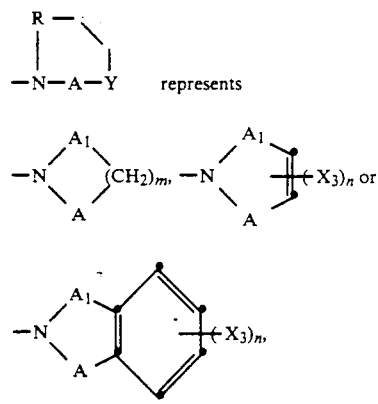

wherein $A_1$ is methylene, carbonyl or sulfonyl; $X_3$ is hydrogen, methyl or halogen; m is 2, 3 or 4; and n is zero, 1 or 2.

Halogen is fluorine, chlorine, bromine or iodine, preferably fluorine and then, in order of preference, chlorine, bromine and iodine. From 1 to 3 halogen atoms may be present as substituents in individual radicals.

Alkyl on its own or as a component of another substituent is to be understood as meaning straight-chain or branched alkyl. Depending on the number of carbon atoms indicated it represents, for example, one of the following groups: methyl, ethyl or an isomer of propyl or butyl, such as, for example, isopropyl, isobutyl, tert.-butyl or sec.-butyl.

Alkenyl is, for example, propenyl-(1), allyl, butenyl-(1), butenyl-(2) or butenyl-(3) and alkynyl is, for example, propynyl-(2), butynyl-(1) or pentynyl-(4).

The invention relates especially to compounds of formula I in which $X_1$ and $X_2$ independently of one another are each hydrogen or together from 1 to 3 fluorine atoms; A is sulfonyl or carbonyl; Y is phenyl substituted by methyl, methoxy, halogen, trifluoromethyl, a $COOCH_3$ group, cyano and/or by nitro; R is hydrogen, methyl, ethyl, trifluoromethyl, allyl or propargyl; and in which the group

represents

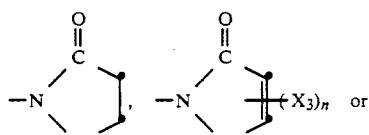 or

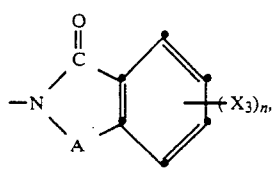

wherein A is sulfonyl or carbonyl; $X_3$ is methyl or halogen; and n is zero, 1 or 2.

The compounds of formula I can be divided into the following groups on the basis of their particular plant-protecting properties:

1. Compounds of formula I in which $X_1$ and $X_2$ independently of one another are each hydrogen or fluorine; A is sulfonyl or carbonyl; Y is phenyl substituted by methyl, methoxy, halogen, trifluoromethyl and/or by a $COOCH_3$ group; R is hydrogen, methyl, ethyl, trifluoromethyl, allyl or propargyl; and in which, furthermore, the group

represents

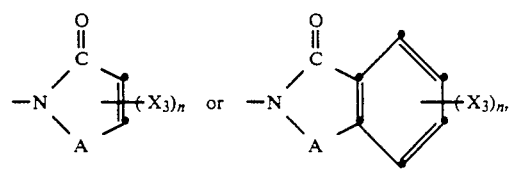

wherein A is sulfonyl or carbonyl; $X_3$ is halogen; and n is zero or 1.

2. Compounds of formula I in which $X_1$ and $X_2$ independently of one another are each hydrogen or fluorine; A is sulfonyl; Y is phenyl substituted by methyl, methoxy, fluorine, chlorine, trifluoromethyl and/or by a COOCH₃ group; R is hydrogen, methyl, trifluoromethyl, allyl or propargyl; and in which, furthermore, the group

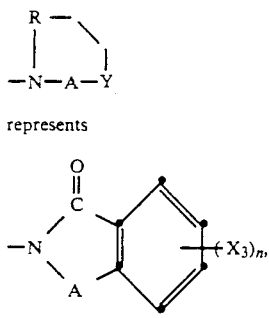

represents

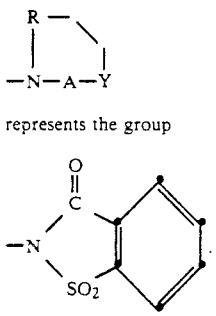

wherein A is sulfonyl; X₃ is chlorine; and n is zero or 1.

3. Compounds of formula I in which X₁ and X₂ independently of one another are each hydrogen or fluorine; A is sulfonyl; Y is phenyl substituted by methyl, fluorine, chlorine and/or by trifluoromethyl; R is hydrogen, methyl, allyl or propargyl; and in which, furthermore, represents the group The following compounds are distinguished by especially advantageous plant-protecting properties:

N-(benzo-1,2,3-thiadiazol-7-ylcarbonyl)-2-sulfobenzoic acid imide (Comp. No. 1.1);

N-4-chlorophenylsulfonylbenzo-1,2,3-thiadiazole-7-carboxylic acid amide (Comp. No. 1.4);

N-2-fluorophenylsulfonylbenzo-1,2,3-thiadiazole-7-carboxylic acid amide (Comp. No. 1.7);

N-allyl-N-phenylsulfonylbenzo-1,2,3-thiadiazole-7-carboxylic acid amide (Comp. No. 1.28);

N-phenylsulfonyl-4-fluorobenzo-1,2,3-thiadiazole-7-carboxylic acid amide (Comp. No. 2.1);

N-4-methylphenylsulfonyl-5-fluorobenzo-1,2,3-thiadiazole-7-carboxylic acid amide (Comp. No. 2.21);

N-phenylsulfonylbenzo-1,2,3-thiadiazole-7-carboxylic acid amide (Comp. No. 4.1);

N-(5-fluorobenzo-1,2,3-thiadiazole-7-carbonyl)-2-sulfobenzoic acid imide (Comp. No. 4.2).

It has now surprisingly been found that the use of compounds of formula I of the invention prevents plants from being attacked by harmful microorganisms and thus guards against damage to plants caused by such attack. A characteristic of the active ingredients of the invention is that the protection of the plants can stem both from the direct action on the plant-damaging microorganisms by means of foliar application or soil application and from the activation and stimulation of the plant's own defence system (immunisation). The great advantage of the compounds of formula I is that it is possible to ensure the continued health of plants treated with these substances also through their own resources without using further microbicidal substances during the vegetation period. Consequently it is possible by using the active ingredients of the invention to avoid the adverse side effects that may occur with direct parasite control using chemical substances, for example on the one hand as a result of damage to the useful plants (phytotoxicity) and on the other hand as a result of causing the harmful microorganisms to develop a resistance; consequently growth of the useful plants is advantageously completely undisturbed.

Owing to the double action of the compounds of formula I of the invention, that is to say on the one hand the direct control of the plant pathogens and on the other hand the increase in the general capacity of plants treated with these active ingredients to defend themselves as a result of immunisation, it is possible to achieve a broadly based protection of plants against disease. The use of the active ingredients of the invention is therefore especially suitable for practical application. Furthermore, the systemic activity peculiar to the compounds of formula I results in the protective effect being extended also to growing parts of the treated plants.

The generally plant-protecting activity of the active ingredients of the invention is effective, for example, against the phytopathogenic fungi belonging to the following classes: Fungi imperfecti (for example Botrytis, Helminthosporium, Fusarium, Septoria, Cercospora and Alternaria); Basidiomycetes (for example of the genera Hemileia, Rhizocotonia, Puccinia); Ascomycetes (for example Venturia, Podosphaera, Erysiphe, Monilinia, Uncinula).

In addition, the active ingredients can be used with particular advantage against the following harmful organisms:

fungi, such as, for example, Oomycetes (for example *Plasmopara viticola, Phytophthora infestans, Peronospora tabacina,* Pseudoperonospora, *Bremia letucae*), Fungi imperfecti (for example *Colletotrichum lagenarium, Piricularia oryzae, Cercospora nicotinae*), Ascomycetes (for example *Venturia inaequalis*);

bacteria, such as, for example, Pseudomonads (*Pseudomonas lachrymans, Pseudomonas tomato, Pseudomonas tabaci*); Xanthomonads (for example *Xanthomonas oryzae, Xanthomonas vesicatoria*); Erwinia (for example *Erwinia amylovora*); and viruses, such as, for example, the Tobacco Mosaic Virus.

The compounds of the invention can be used to protect plants of various useful crops.

The following species of plants, for example, are suitable for the use within the scope of the invention of compounds of formula I of the invention: cereals (wheat, barley, rye, oats, rice, sorghum and related crops); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (cucumber, pumpkin, melons); fibre plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocados, cinnamon, camphor), or plants such as maize, tobacco, nuts, coffee, sugar cane, tea, vines, hops, bananas and natural rubber plants, as well as ornamentals (flowers, shrubs, deciduous trees and conifers). This list does not constitute a limitation.

The following plants are to be regarded as especially suitable target crops for the application of the process of the invention: cucumber, tobacco, vines, rice, pepper, potatoes, tomatoes, wheat, barley, pears and apples.

The compounds of formula I are obtained by reacting:

a benzothiadiazole compound of formula II

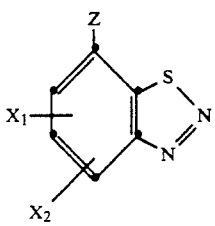
(II)

in the presence of a base and optionally with a catalyst, such as, for example, 4-dialkylaminopyridine, especially 4-dimethylaminopyridine, in an inert solvent, with an amide compound of formula III

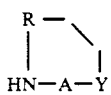
(III)

in which formulae Z represents the radicals COOH, HalCO, $COOC_1-C_5$alkyl

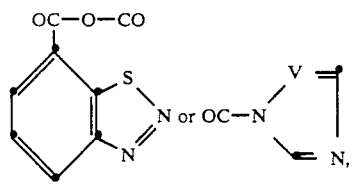

V is CH or N and Hal is halogen, and $X_1$, $X_2$, A, Y and R are as defined for formula I. The reaction is carried out at temperatures of from $-10°$ to $200°$ C., preferably from $0°$ to $100°$ C.

According to a further process for the preparation of compounds of formula I the following reactions are carried out: a compound of formula II

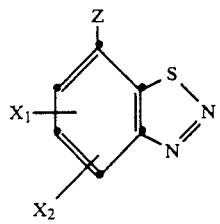
(II)

is first of all converted by reaction with an amino compound of formula IV

 (IV)

in an inert solvent and in the presence of a base, into an amide compound of formula V

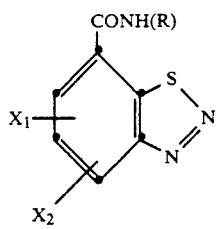
(V)

and this is then reacted, in an inert solvent and in the presence of a base, with an acid derivative of formula VI

Z'—A—Y (VI)

in which formulae Z' represents the radical OH, Hal, $OC_1-C_5$alkyl or

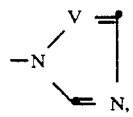

or the radical Z'—A represents

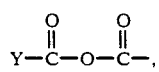

V is CH or N and Hal is halogen, and $X_1$, $X_2$, A, Y and R are as defined for formula I. The reactions are carried out at temperatures of from $-10°$ to $200°$ C., preferably from $0°$ to $100°$ C.

Compounds of formula II in which Z is COOH can be obtained either as described in the literature (cf. J. Chem. Soc. 1971, 3997) or advantageously in accordance with the Preparatory Examples given hereinafter. Acid halides that fall within the scope of formula II are produced from the corresponding free carboxylic acids, for example with thionyl chloride, phosgene, oxalyl chloride or 1-chloro-N,N-2-trimethylpropenylamine (cf. L. Ghosez, J. Chem. Soc. Comm. 1979, 1180). Acid anhydrides that fall within the scope of formula II can be obtained, for example, by heating the corresponding free acid with acetic anhydride. Imidazolides and triazolides that fall within the scope of formula II are obtained from the carboxylic acids by reaction with N,N-carbonyldiimidazole or N,N-carbonylditriazole (cf. H. A. Staab, Angew. Chemie 1964, 132).

Suitable bases are organic and inorganic bases, for example tertiary amines, such as trialkylamines (trimethylamine, triethylamine, tripropylamine etc.), pyridine bases, (pyridine, 4-dimethylaminopyridine, 4-pyrrolidylaminopyridine, collidine), oxides and hydroxides, carbonates and hydrogen carbonates of alkali metals and alkaline earth metals, and also hydrides, such as, for example, sodium hydride or calcium hydride, or alkyllithium compounds, such as, for example, n-butyllithium.

Suitable solvents and diluents that are inert towards the reactions are used as reaction media in accordance with the respective reaction conditions. The following may be mentioned as examples: aliphatic and aromatic hydrocarbons, such as benzene, toluene, xylenes, petroleum ether; halogenated hydrocarbons, such as chlorobenzene, methylene chloride, ethylene chloride, chloroform, carbon tetrachloride, tetrachloroethylene; ethers and ethereal compounds, such as dialkyl ethers (diethyl ether, diisopropyl ether, tert.-butyl methyl ether etc.), anisole, dioxane, tetrahydrofuran; nitriles, such as acetonitrile, propionitrile; N,N-dialkylated amides, such as dimethylformamide; ketones, such as acetone, diethyl ketone, methyl ethyl ketone; and also mixtures of such solvents with one another.

Amino compounds of formula III are known or can be prepared according to methods known to the person skilled in the art.

A compound of formula V in which R is hydrogen can be prepared by reacting a carboxylic acid ester that falls within the scope of formula II, preferably the methyl ester, with from 1 to 100 equivalents, preferably from 1 to 30 equivalents, of liquid ammonia in an autoclave at $1 \cdot 10^5$ Pa to $100 \cdot 10^5$ Pa, preferably $5 \cdot 10^5$ Pa to $60 \cdot 10^5$ Pa, at from 0° to 160° C., preferably from 20° to 120° C., in an inert solvent.

A compound of formula V in which R is hydrogen can be furthermore be prepared by reacting an acid halide that falls within the scope of formula II with hexamethyldisilazane of formula $[(CH_3)_2Si]_2NH$, or an analogous silylamine, in an inert solvent at temperatures of from $-10°$ to 80° C., preferably from 0° to 40° C., and then subjecting the mixture to hydrolysis, for example with an alcohol, such as methanol, and a dilute mineral acid, for example sulfuric acid (cf. Synthetic Communications 1985, 519).

The microbicidal compositions that are used within the scope of the invention for protecting plants against disease and that contain the compounds of formula I as active ingredients are to be considered as part of the invention.

The active ingredients of formula I are normally used in the form of compositions and can be applied to the plant or the locus thereof, simultaneously or in succession, with further active ingredients. These further active ingredients can be fertilisers or micronutrient donors or other preparations that influence plant growth. They can, however, also be selective herbicides, insecticides, fungicides, bactericides, nematicides, molluscicides or mixtures of several of these preparations, if desired together with further carriers, surfactants or other application-promoting adjuvants customarily employed in the art of formulation.

Suitable carriers and adjuvants can be solid or liquid and correspond to the substances ordinarily employed in formulation technology, e.g. natural or regenerated mineral substances, solvents, dispersants, wetting agents, tackifiers, thickeners, binders or fertilisers.

One method of applying an active ingredient of formula I or an agrochemical composition containing at least one of those active ingredients is application to the plant (foliar application). The active ingredients of formula I can, however, also penetrate the plant through the roots via the soil (soil application) if the locus of the plant is impregnated with a liquid formulation, or if the compounds are applied in solid form to the soil, for example in granular form. The compounds of formula I may, however, also be applied to seeds (coating), either by impregnating the seeds with a liquid formulation of the active ingredient or coating them with a solid formulation (dressing). In addition, in special cases further types of application are possible, for example the selective treatment of the plant stems or buds.

The compounds of formula I are used in unmodified form or, preferably, together with the adjuvants conventionally employed in the art of formulation, and are for this purpose formulated in known manner e.g. into emulsifiable concentrates, coatable pastes, directly sprayable or dilutable solutions, dilute solutions, wettable powders, soluble powders, dusts, granulates, and also encapsulations in e.g. polymer substances. As with the nature of the compositions, the methods of application, such as spraying, atomising, dusting, scattering, coating or pouring, are chosen in accordance with the intended objectives and the prevailing circumstances. Advantageous rates of application are normally from 50 g to 5 kg of active ingredient (a.i.) per hectare, preferably from 100 g to 2 kg a.i./ha, most preferably from 100 g to 600 g a.i./ha.

The formulations, i.e. the compositions, preparations or mixtures containing the compound (active ingredient) of formula I and, where appropriate, a solid or liquid adjuvant, are prepared by homogeneously mixing and/or grinding the active ingredients with extenders, e.g. solvents, solid carriers and, where appropriate, surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils, such as epoxidised coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are, for example, calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Cationic surfactants are especially quaternary ammonium salts that contain as N-substituent at least one alkyl radical having from 8 to 22 carbon atoms and as further substituents lower, unsubstituted or halogenated alkyl, benzyl or hydroxy-lower alkyl radicals.

Both so-called water-soluble soaps and also water-soluble synthetic surface-active compounds are suitable anionic surfactants.

Suitable soaps are the alkali metal salts, alkaline earth metal salts or unsubstituted or substituted ammonium salts of higher fatty acids ($C_{10}-C_{22}$), e.g. the sodium or potassium salts of oleic or stearic acid or of natural fatty acid mixtures which can be obtained e.g. from coconut oil or tallow oil.

Suitable synthetic surfactants are especially fatty alcohol sulfonates, fatty alcohol sulfates, sulfonated benzimidazole derivatives or alkylsulfonates. The fatty alcohol sulfonates or sulfates are usually in the form of alkali metal salts, alkaline earth metal salts or unsubstituted or substituted ammonium salts and contain an alkyl radical having from 8 to 22 carbon atoms.

Non-ionic surfactants are preferably polyglycol ether derivatives of aliphatic or cycloaliphatic alcohols, saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

The compositions may also contain further auxiliaries, such as stabilisers, antifoams, viscosity regulators, binders, tackifiers as well as fertilisers or other active ingredients for achieving special effects.

The agrochemical compositions usually contain 0.1 to 99 % by weight, preferably 0.1 to 95 % by weight, of a compound of formula I, 99.9 to 1 % by weight, preferably 99.8 to 5 % by weight, of a solid or liquid adjuvant, and 0 to 25 % by weight, preferably 0.1 to 25 % by weight, of a surfactant.

The following Examples serve to illustrate the invention without implying any limitation.

1. PREPARATION EXAMPLES 1. Preparation of N-(phenylsulfonyl)-benzo-1,2,3-thiadiazole-7-carboxylic acid amide

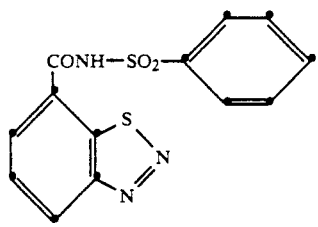

3.2 g of benzenesulfonamide are introduced at from 0°–5° C. into 50 ml of abs. pyridine and, while stirring at that temperature, a solution of 3.9 g of benzo-1,2,3-thiadiazole-7-carboxylic acid chloride in 20 ml of methylene chloride is added dropwise. The mixture is stirred overnight and then poured onto ice-water, rendered slightly acidic with hydrochloric acid and extracted with methylene chloride, and the extracts are washed with water, dried and concentrated by evaporation. The residue is dissolved warm in tetrahydrofuran, treated with some silica gel, filtered, concentrated by evaporation and then recrystallised from tetrahydrofuran/hexane. The title compound resulting melts at 231°–233° C.

2. Preparation of N-benzo-1,2,3-thiadiazol-7-yl)-carbonyl-2-sulfobenzoic acid imide

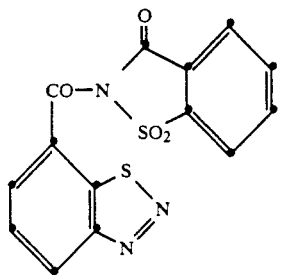

After the addition of a spatula tip of 4-dimethylaminopyridine to a suspension of 4 g of the sodium salt of saccharin in 60 ml of methylene chloride, a solution of 3.9 g of benzo-1,2,3-thiadiazole-7-carboxylic acid chloride in 20 ml of methylene chloride is added dropwise at a maximum of 20° C. The mixture is stirred overnight at room temperature and the next day the suspension is poured onto ice-water and extracted with ethyl acetate. The extracts are washed with dilute sodium hydrogen carbonate solution and water, dried and concentrated by evaporation. The residue is recrystallised from tetrahydrofuran/hexane to yield the title compound having a melting point of 173°–175° C.

3. preparation of benzo-1,2,3-thiadiazole-7-carboxylic acid amide (intermediate product)

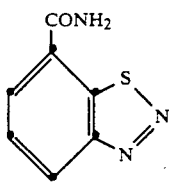

In an autoclave, under pressure and at room temperature, 17 g of ammonia is passed into a solution of 19.4 g of benzo-1,2,3-thiadiazole-7-carboxylic acid methyl ester in 70 ml of tetrahydrofuran. The solution is then heated and maintained at 80°–90° C. for approximately 20 hours, an internal pressure of $55 \cdot 10^5$ Pa max. building up. Partial concentration by evaporation is then carried out and the resulting precipitate is filtered off, washed with cold tetrahydrofuran and dried. 14.9 g of beige crystals having a melting point of 270°–272° C. are obtained.

4. Preparation of N-(benzo-1,2,3-thiadiazole-7-carbonyl)-pyrrolidone-2

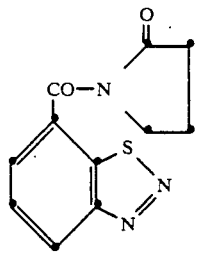

0.576 ml of trimethylchlorosilane is added dropwise at a maximum of 15° C., with stirring and under a nitrogen atmosphere, to a solution, prepared at 10° C., of 0.348 ml of 2-pyrrolidone and 0.653 ml of triethylamine in 10 ml of tetrahydrofuran. The mixture is then stirred for 1 hour towards room temperature and subsequently, with renewed cooling with ice-water, a solution of 0.9 g of benzo-1,2,3-thiadiazole-7-carboxylic acid chloride in 5 ml of tetrahydrofuran is added dropwise over a period of 10 minutes at a maximum of 20° C. The mixture is stirred overnight at room temperature, ice-water and ethyl acetate are added, the organic phase is separated off and the aqueous phase is extracted a further twice with ethyl acetate. The combined extracts are washed with sodium hydrogen carbonate solution and water, dried over sodium sulfate and filtered over a small amount of silica gel. The filtrate is concentrated by evaporation and the residue is dissolved in tetrahydrofuran/hexane and allowed to crystallise. 0.7 g of the title compound having a melting point of 146°–147° C. is obtained.

5. Preparation of the symmetrical anhydride of 1,2,3-benzothiadiazole-7carboxylic acid

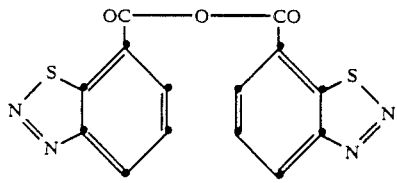

3 g of 1,2,3-benzothiadiazole-7-carboxylic acid are boiled under reflux for 24 hours in 50 ml of acetic anhydride. The dilute suspension is then concentrated by evaporation in vacuo, and the solid residue is suspended in ether and filtered off. 4.3 g of anhydride having a melting point of 117°–119° C. are obtained. The same compound is obtained, for example, also by heating the carboxylic acid with bis-(2-oxo-3-oxazolidinyl)-phosphinic acid chloride in dry tetrahydrofuran (cf. Synthesis 1981, 616).

6. Preparation of 7-methoxycarbonylbenzo-1,2,3-thiadiazole (intermediate product)

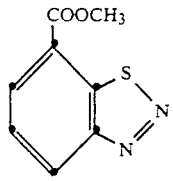

a) 100 g (0.35 mole) of 2-benzylthio-3,5-diaminobenzoic acid methyl ester are added in portions to 250 ml of concentrated hydrochloric acid and 110 ml of water and the mixture is stirred at room temperature for 1.5 hours. The mixture is then cooled to $-5°$ C. and, with stirring, a solution of 48.5 g (0.70 mole) of sodium nitrite in 210 ml of water is added dropwise over a period of 2.5 hours. The stirring is continued for a further 2 hours at 0° C. 190 ml of 50 % hypophosphorous acid are then added dropwise over a period of 2½ hours. The temperature is then allowed to rise to 20° C. for 19 hours. The product obtained is filtered off, washed with water and dried.

For purification, the product is dissolved in ethyl acetate/methylene chloride, filtered through silica gel, evaporated, and crystallised by the addition of hexane. Yield: 44.4 g (65 % of the theoretical amount); m.p. 132° C.

b) 576 g (2 moles) of 3,5-diamino-2-benzylthiobenzoic acid methyl ester are dissolved in 500 ml of 1,4-dioxane and, with stirring and cooling at from 0° to 5° C., added dropwise to 5N hydrochloric acid (3 l). The fine suspension is then cooled to from $-17°$ to $-20°$ C. and, over a period of 1.25 hours, 294 g of sodium nitrite in 500 ml of water are added dropwise below the surface level. With further stirring, the internal temperature is allowed to rise to $-5°$ C. over a period of 1 hour and maintained at that temperature for 2 hours. The suspension is then cooled to $-15°$ C. and, with stirring, is added in portions to hypophosphorous acid (1.1 l) that has been cooled to from $-10°$ to $-15°$ C., nitrogen being evolved. When the addition is complete, the internal temperature is allowed to rise to room temperature over a period of 5–6 hours, the precipitate formed is filtered off, stirred with 2.5 l of methylene chloride, and filtered off again from the undissolved portion, and the filtrate is separated from the water. The organic phase is then dried over sodium sulfate, stirred with 300 g of silica gel, filtered again, and subsequently washed with methylene chloride, and the filtrate is concentrated by evaporation. The residue is recrystallised from methanol to yield a total of 244.8 g (63.1 % of the theoretical amount) of beige crystals having a melting point of 130°–133° C.

TABLE 1

| Comp. No. | Q | R | physical data |
|---|---|---|---|
| 1.1 | H | H | m.p. 231–233° C. |
| 1.2 | 2,3-di-Cl | H(pyridinium salt) | m.p. 256–259° C. |
| 1.3 | H | CH$_3$ | |
| 1.4 | 4-Cl | H | m.p. 250–252° C. |
| 1.5 | 2,4-di-Cl | H | m.p. 279–280° C. |
| 1.6 | 2,4,6-tri-Cl | H | m.p. 248–249° C. |
| 1.7 | 2-F | H | m.p. 270–272° C. |
| 1.8 | 4-F | H | |
| 1.9 | 2-CH$_3$-4-Cl | H | |
| 1.10 | 2,6-Di-Cl | H | |
| 1.11 | 3-CF$_3$ | H | |
| 1.12 | 3-NO$_2$-4-Cl | H | |
| 1.13 | 3-Cl | H | |
| 1.14 | 2-CH$_3$ | H | |
| 1.15 | 2-CH$_2$OCOCH$_3$ | H | |
| 1.16 | 2-COOC$_2$H$_5$ | H | |
| 1.17 | 2-F | Me | |
| 1.18 | 4-F | CH$_2$—CH=CH$_2$ | |
| 1.19 | 2,4-Di-F | H | |
| 1.20 | 3-NO$_2$ | H | m.p. 273–274° C. |
| 1.21 | 3-Cl | C$_2$H$_5$ | |
| 1.22 | 3-CF$_3$ | n-C$_4$H$_9$ | |
| 1.23 | H | C$_2$H$_5$ | |
| 1.24 | H | C$_3$H$_7$ | |
| 1.25 | 4-CH$_3$ | H | |
| 1.26 | 4-CH$_3$ | CH$_3$ | |
| 1.27 | 2-CF$_3$-4-Cl | H | |
| 1.28 | H | CH$_2$—CH=CH$_2$ | m.p. 100–102° C. |
| 1.29 | H | CH$_2$—C≡CH | |
| 1.30 | H | —CH$_2$CH=CH—CH$_3$ | |
| 1.31 | H | —CH$_2$C≡C—CH$_3$ | |
| 1.32 | H | —CH$_2$CH=CH—C$_2$H$_5$ | |
| 1.33 | 3-CN | H | |
| 1.34 | 2-COOCH$_3$ | CH$_3$ | |
| 1.35 | 2-CH$_2$OC$_3$H$_{7-n}$ | H | |
| 1.36 | 4-OCH$_3$ | H | m.p. 230–231° C. |
| 1.37 | 4-OC$_2$H$_5$ | H | |
| 1.38 | 2-C$_2$H$_5$ | H | |
| 1.39 | CH$_2$CCl$_3$ | H | |

TABLE 2

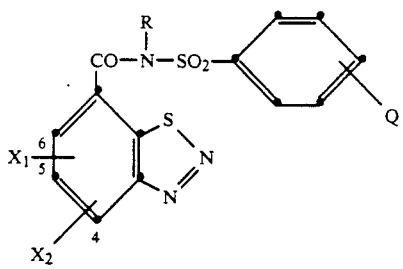

| Comp. No. | Q | $X_1$ | $X_2$ | R | physical data |
|---|---|---|---|---|---|
| 2.1 | H | 4-F | | H | |
| 2.2 | H | 6-F | | H | m.p. 157-158° C. |
| 2.3 | H | 5-F | 4-F | H | |
| 2.4 | H | 5-F | H | $CH_2-CH=CH_2$ | |
| 2.5 | H | 5-F | H | H | |
| 2.6 | H | 5-Cl | H | H | |
| 2.7 | H | 5-Br | H | H | |
| 2.8 | H | 5-I | H | H | |
| 2.9 | 2,3-di-Cl | 5-I | H | H | |
| 2.10 | 2,3-di-Cl | 5-F | H | H* | m.p. 218-220° C. |
| 2.11 | 4-O—$CH_3$ | 5-F | H | H | m.p. 196-198° C. |
| 2.12 | 4-F | 5-F | H | H | |
| 2.13 | 3-F | 6-F | H | H | |
| 2.14 | 2,6-di-Cl | 5-F | 6-F | H | |
| 2.15 | 2,3-di-Cl | 5-Br | H | $CH_3$ | |
| 2.16 | 4-O—$C_2H_5$ | 5-F | H | $CH_3$ | |
| 2.17 | 2-$CH_2Cl$ | 5-F | H | $CH_3$ | |
| 2.18 | 2-$CH_2OC(O)CH_3$ | 5-F | H | $CH_3$ | |
| 2.19 | 4-$CH_3$ | 5-F | H | $CH_3$ | |
| 2.20 | 4-Cl | 5-F | H | H | m.p. 165-167° C. |
| 2.21 | 4-$CH_3$ | 5-F | H | H | m.p. 231-233° C. |
| 2.22 | 4-F | 6-F | H | H | m.p. 207-208° C. |

*(pyridinium salt)

TABLE 3

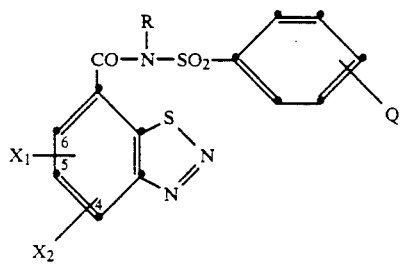

| Comp. No. | Q | $X_1$ | $X_2$ | R | physical data |
|---|---|---|---|---|---|
| 3.1 | H | H | H | H | |
| 3.2 | 4-$CH_3$ | 5-F | H | H | |
| 3.3 | 4-Cl | 6-F | H | H | |
| 3.4 | 4-$OC_2H_5$ | H | H | H | |
| 3.5 | H | H | H | $CH_3$ | |
| 3.6 | H | H | H | $CH_2-CH=CH_2$ | |
| 3.7 | H | H | H | $CH_2-C\equiv CH$ | |
| 3.8 | 2,6-di-Cl | 5-F | H | $CH_2-CH=CH_2$ | |
| 3.9 | 2,6-di-Cl | 5-F | H | $C_2H_5$ | |
| 3.10 | H | 5-F | 6-F | H | |
| 3.11 | 3-$CF_3$ | H | H | H | |
| 3.12 | 3-$NO_2$ | H | H | H | |
| 3.13 | 2-F | H | H | H | |
| 3.14 | 3-$CF_3$ | 5-Cl | H | H | |
| 3.15 | H | 5-Br | H | H | |
| 3.16 | 2-$CH_3$ | H | H | H | |
| 3.17 | 2,4,6-tri-Cl | H | H | H | |
| 3.18 | 2,3-di-Cl | H | H | H | |
| 3.19 | 2-COO—$CH_3$ | H | H | $CH_3$ | |
| 3.20 | H | 5-I | H | $CH_3$ | |

TABLE 4

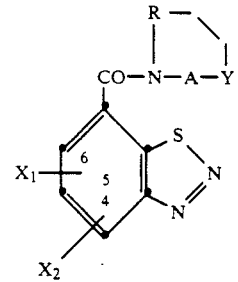

| Comp. No. | —N—A—Y | $X_1$ | $X_2$ | physical data |
|---|---|---|---|---|
| 4.1 | ![structure] | H | H | m.p. 173-175° C. |
| 4.2 | ![structure] | 5-F | H | m.p. 177-179° C. |

TABLE 4-continued
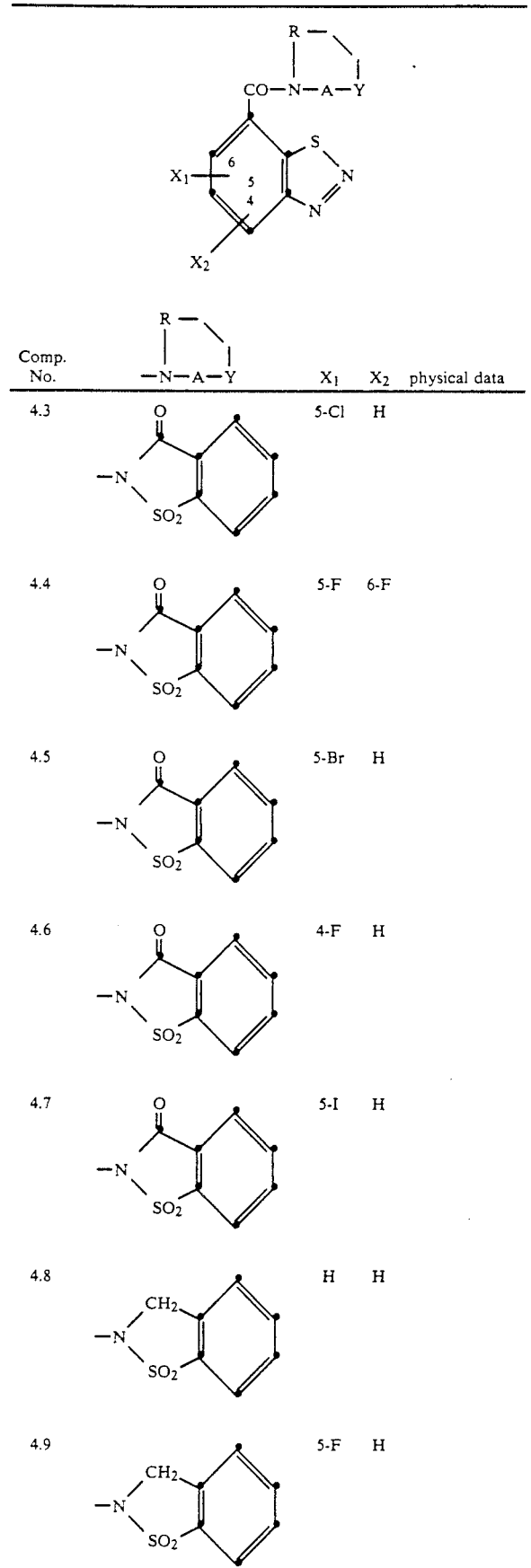
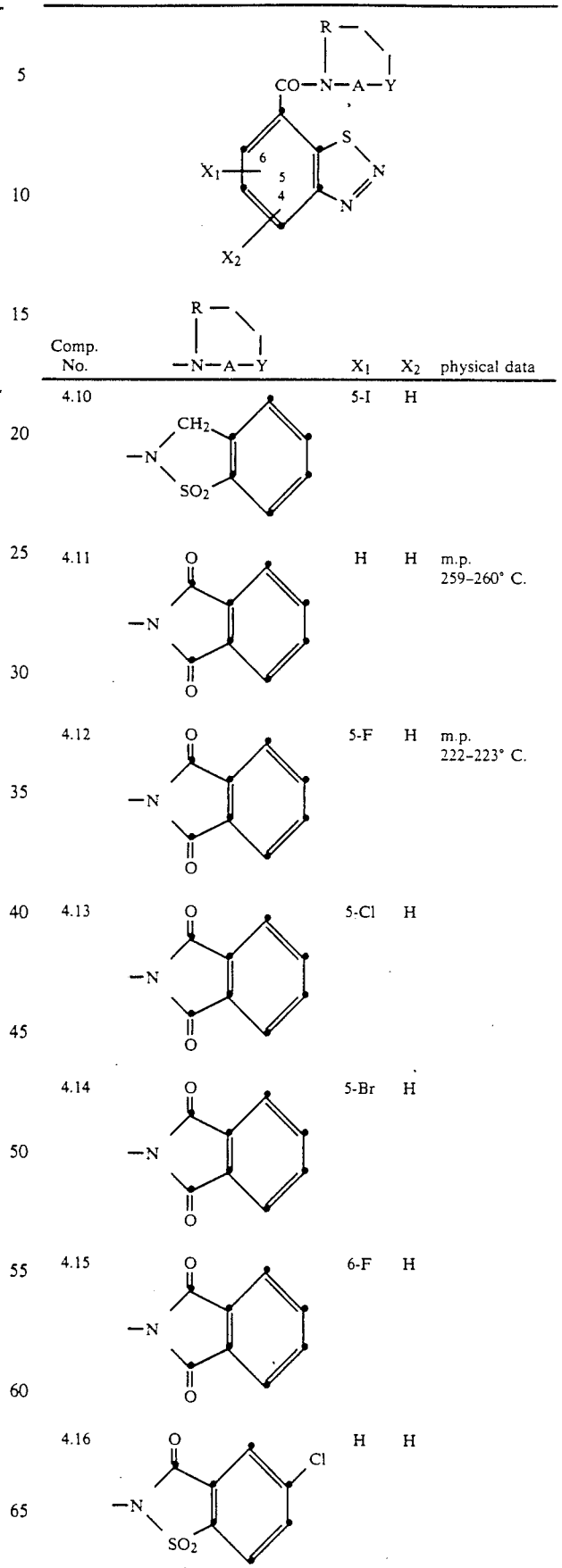

TABLE 4-continued

General structure: benzothiadiazole with CO-N(R)-A-Y substituent, positions labeled 4, 5, 6, with X₁ at 6 and X₂ at position shown.

| Comp. No. | -N-A-Y (with R) | $X_1$ | $X_2$ | physical data |
|---|---|---|---|---|
| 4.17 | -N-pyrrolidinone (5-membered, C=O) | H | H | |
| 4.18 | -N-piperidinone (6-membered, C=O) | H | H | |
| 4.19 | -N-azepanone (7-membered, C=O) | H | H | |
| 4.20 | -N-azepanone (7-membered, C=O) | 5-F | H | |
| 4.21 | -N-azepanone (7-membered, C=O) | 6-F | H | |
| 4.22 | -N-azepanone (7-membered, C=O) | 5-Br | H | |
| 4.23 | -N-glutarimide (6-membered, two C=O) | H | H | m.p. 202-203° C. |
| 4.24 | -N-maleimide-type (6-membered, two C=O with C=C) | H | H | |
| 4.25 | -N-sulfonyl ring (C=O, SO₂) | H | H | |
| 4.26 | -N-(3,4-dichloromaleimide type, two C=O, two Cl) | H | H | |
| 4.27 | -N-(chloromaleimide type, two C=O, one Cl) | 5-F | H | |
| 4.28 | -N-(dimethylmaleimide type, two C=O, two Me) | H | H | |
| 4.29 | -N-(6-membered, two C=O, C=C) | H | H | |

2. Formulation Examples for active ingredients of formula I (throughout, percentages are by weight)

| 2.1. Wettable powders | (a) | (b) | (c) |
|---|---|---|---|
| active ingredient from the Tables | 25% | 50% | 75% |
| sodium lignosulfonate | 5% | 5% | — |
| sodium laurylsulfate | 3% | — | 5% |
| sodium diisobutylnaphthalene-sulfonate | — | 6% | 10% |
| octylphenol polyethylene glycol ether (7-8 moles of ethylene oxide) | — | 2% | — |
| highly dispersed silicic acid | 5% | 10% | 10% |

| 2.1. Wettable powders | (a) | (b) | (c) |
|---|---|---|---|
| kaolin | 62% | 27% | — |

The active ingredient is mixed with the adjuvants and the mixture is homogeneously ground in a suitable mill, affording wettable powders which can be diluted with water to give suspensions of the desired concentration.

| 2.2. Emulsifiable concentrate | |
|---|---|
| active ingredient from the Tables | 10% |
| octylphenol polyethylene glycol ether (4–5 moles of ethylene oxide) | 3% |
| calcium dodecylbenzenesulfonate | 3% |
| castor oil polyglycol ether (35 moles of ethylene oxide) | 4% |
| cyclohexanone | 30% |
| xylene mixture | 50% |

Emulsions of any required concentration can be obtained from this concentrate by dilution with water.

| 2.3. Dusts | (a) | (b) |
|---|---|---|
| an active ingredient from the Tables | 5% | 8% |
| talcum | 95% | — |
| kaolin | — | 92% |

Ready-for-use dusts are obtained by mixing the active ingredient with the carriers and grinding the mixture in a suitable mill.

| 2.4. Extruder granulate | |
|---|---|
| an active ingredient from the Tables | 10% |
| sodium lignosulfonate | 2% |
| carboxymethylcellulose | 1% |
| kaolin | 87% |

The active ingredient is mixed and ground with the adjuvants, and the mixture is moistened with water. The mixture is extruded and then dried in a stream of air.

| 2.5. Coated granulate | |
|---|---|
| an active ingredient from the Tables | 3% |
| polyethylene glycol (MW 200) | 3% |
| kaolin | 94% |

(MW = molecular weight)

The finely ground active ingredient is uniformly applied, in a mixer, to the kaolin moistened with polyethylene glycol. Non-dusty coated granulates are obtained in this manner.

| 2.6 Suspension concentrate | |
|---|---|
| an active ingredient from the Tables | 40% |
| ethylene glycol | 10% |
| nonylphenol polyethylene glycol ether (15 moles of ethylene oxide) | 6% |
| sodium lignosulfonate | 10% |
| carboxymethylcellulose | 1% |
| 37% aqueous formaldehyde solution | 0.2% |
| silicone oil in the form of a 75% aqueous emulsion | 0.8% |

| 2.6 Suspension concentrate | |
|---|---|
| water | 32% |

The finely ground active ingredient is intimately mixed with the adjuvants, giving a suspension concentrate from which suspensions of any desired concentration can be obtained by dilution with water.

3. Biological Examples

EXAMPLE 3.1

Action against Colletotrichum lagenarium on Cucumis sativus L.

a) After 2 weeks' cultivation, cucumber plants are sprayed with a spray mixture prepared from a wettable powder formulation of the test compound (concentration: 200 ppm). After 48 hours the plants are infected with a spore suspension ($1.5 \times 10^5$ spores/ml) of the fungus and incubated for 36 hours at high humidity and a temperature of 23° C. Incubation is then continued at normal humidity and at from 22° C. to 23° C.

The protective action is assessed on the basis of the fungal attack 7 to 8 days after infection.

b) After 2 weeks' cultivation, cucumber plants are treated by soil application with a spray mixture prepared from a wettable powder formulation of the test compound (concentration: 60 or 20 ppm based on the volume of soil). After 48 hours the plants are infected with a spore suspension ($1.5 \times 10^5$ spores/ml) of the fungus and incubated for 36 hours at high humidity and a temperature of 23° C. Incubation is then continued at normal humidity and at 22° C.

The protective action is assessed on the basis of the fungal attack 7 to 8 days after infection.

c) After 2 weeks' cultivation, cucumber plants are sprayed with a spray mixture prepared from a wettable powder formulation of the test compound (concentration: 200 ppm)

After 3 weeks the plants are infected with a spore suspension ($1.5 \times 10^5$ spores/ml) of the fungus and incubated for 36 hours at high humidity and a temperature of 23° C. Incubation is then continued at normal humidity and at from 22° to 23° C.

The protective action is assessed on the basis of the fungal attack 7 to 8 days after infection.

Compounds from Tables 1 to 4 exhibited good activity in tests (a) and (b). For example, compound 4.1 confined fungal attack to 0 to 20 %. On the other hand, Colletotrichum attack was 100 % on untreated and infected control plants.

EXAMPLE 3.2

Action against Phytophthora infestans on tomato plants a) After 3 weeks' cultivation, tomato plants are sprayed with a spray mixture (0.02 % active ingredient) prepared from a wettable powder formulation of the test compound. After 24 hours the treated plants are infected with a sporangia suspension of the fungus. The fungal attack was evaluated after incubating the infected plants for 5 days at 90–100 % relative humidity and 20° C.

b) After a cultivation period of 3 weeks tomato plants are watered with a spray mixture (0.006 % active ingredient based on the volume of soil) prepared from a wettable powder formulation of the test compound.

Care is taken that the spray mixture does not come into contact with the parts of the plants that are above the soil. After 48 hours the treated plants are infected with a sporangia suspension of the fungus. The fungal attack is evaluated after incubating the infected plants for 5 days at 90-100 % relative humidity and 20° C.

Compounds from Tables 1 to 4 exhibited a good protective action against the Phytophthora fungus. For example, compounds 1.1, 1.2 and 4.1 confined fungal attack to 0 to 20 %. On the other hand, Phytophthora attack was 100% on untreated and infected control plants.

EXAMPLE 3.3

Action against Plasmopara viticola on vines a) Vine seedlings at the 4 to 5 leaf stage are sprayed with a spray mixture (0.02 % active ingredient) prepared from a wettable powder formulation of the test compound. After 24 hours the treated plants are infected with a sporangia suspension of the fungus. Fungal attack is evaluated after incubation for 6 days at 95-100 % relative humidity and 20° C.

b) Vine seedlings at the 4 to 5 leaf stage are infected with a sporangia suspension of the fungus. After having been incubated for 24 hours in a humidity chamber at 95-100 % relative humidity and 20° C., the infected plants are dried and sprayed with a spray mixture (0.06 % active ingredient) prepared from a wettable powder formulation of the test compound. After the spray coating has dried the treated plants are placed in the humidity chamber again. The fungal attack is evaluated 6 days after infection.

Compounds from Tables 1 to 4, for example 1.20, exhibited a good protective action against Plasmopara viticola (0-20 % attack). On the other hand, Plasmopara attack was 100 % on untreated and infected control plants.

EXAMPLE 3.5

Action against Pyricularia oryzae on rice plants a) After 2 weeks' cultivation, rice plants are sprayed with a spray mixture (0.02 % active ingredient) prepared from a wettable powder formulation of the test compound. After 48 hours, the treated plants are infected with a conidia suspension of the fungus. Evaluation of fungal attack is made after incubation for 5 days at 95-100 % relative humidity and 24° C.

b) 2 week-old rice plants are watered with a spray mixture (0.006 % active ingredient based on the volume of soil) prepared from a wettable powder formulation of the test compound. The pots are then filled with water until the lowest parts of the stalks of the rice plants stand in water. After 96 hours the treated rice plants are infected with a conidia suspension of the fungus. Evaluation of fungal attack is made after incubation of the infected plants for 5 days at 95-100 % relative humidity and approximately 24° C.

Rice plants that had been treated with a spray mixture containing one of the compounds from Tables 1 to 4 as active ingredient exhibited only slight fungal attack compared with untreated control plants (100% attack). For example in test (a) compounds 1.1 and 1.2, and in test (b) compounds 1.1, 1.2 and 4.1 confined fungal attack to 0 to 20%.

EXAMPLE 3.6

Action against Xanthomonas oryzae on rice (Oryza sativa)

a) After 3 weeks' cultivation in a greenhouse, rice plants of the variety "Calora" or "S6" are sprayed with the test substance in the form of a spray mixture (0.02 % active ingredient). After this spray coating has dried for 1 day the plants are placed in a climatic chamber at 24° C. and 75-85% relative humidity and infected. The infection is carried out by cutting off the leaf tips with shears that have beforehand been immersed in a suspension of Xanthomonas oryzae. After an incubation period of 10 days the cut leaves that have been attacked become shrivelled, roll up and become necrotic. The residual activity of the test substance is evaluated on the basis of the extent of these disease symptoms.

b) After a cultivation period of 3 weeks in a greenhouse, rice plants of the variety "Calora" or "S6" are watered with a suspension of the test substance (0.006 % active ingredient based on the volume of soil). Three days after this treatment the plants are placed in a climatic chamber at 24° C. and 75-85% relative humidity and infected. The infection is carried out by cutting off the leaf tips with shears that have beforehand been immersed in a suspension of Xanthomonas oryzae. After an incubation period of 10 days the cut leaves that have been attacked become shrivelled, roll up and become necrotic. The systemic activity of the test substance is evaluated on the basis of the extent of these disease symptoms.

Compounds from Tables 1 to 4 exhibited a good protective action against Xanthomonas oryzae.

What is claimed is:

1. Compounds of formula I in which $X_1$ and $X_2$ independently of one another are each hydrogen or together 1 to 3 halogen atoms; A is sulfonyl or carbonyl; Y is phenyl or phenyl substituted by $C_1$-$C_2$alkyl, $C_1$-$C_2$alkoxy, halogen, $C_1$-$C_2$haloalkyl, $C_1$-$C_2$alkoxycarbonyl, $C_1$-$C_3$alkanoyloxymethyl, cyano and/or by nitro; R is hydrogen, $C_1$-$C_4$alkyl, $C_1$-$C_4$haloalkyl, $C_3$-$C_5$alkenyl or $C_3$-$C_5$alkynyl; and in which, furthermore, the group

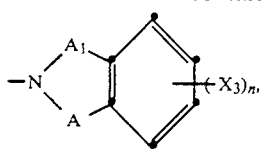

wherein A₁ is methylene, carbonyl or sulfonyl; X₃ is hydrogen, methyl or halogen; m is 2, 3 or 4; and n is zero, 1 or 2.

2. Compounds of formula I according to claim 1 in which $X_1$ and $X_2$ independently of one another are each hydrogen or together from 1 to 3 fluorine atoms; A is sulfonyl or carbonyl; Y is phenyl substituted by methyl, methoxy, halogen, trifluoromethyl, a COOCH₃ group, cyano and/or by nitro; R is hydrogen, methyl, ethyl, trifluoromethyl, allyl or propargyl; and in which, furthermore, the group

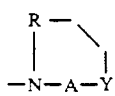

represents

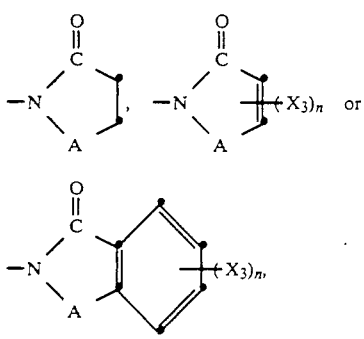

wherein A is sulfonyl or carbonyl; X₃ is methyl or halogen; and n is zero, 1 or 2.

3. Compounds of formula I according to claim 1 in which $X_1$ and $X_2$ independently of one another are each hydrogen or fluorine; A is sulfonyl or carbonyl; Y is phenyl substituted by methyl, methoxy, halogen, trifluoromethyl and/or by a COOCH₃ group; R is hydrogen, methyl, ethyl, trifluoromethyl, allyl or propargyl; and in which, furthermore, the group

represents

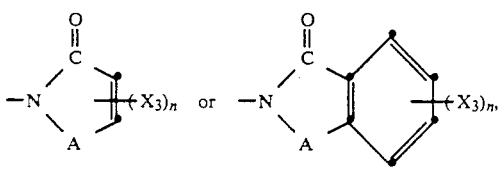

wherein A is sulfonyl or carbonyl; X₃ is halogen; and n is zero or 1.

4. Compounds of formula I according to claim 1 in which $X_1$ and $X_2$ independently of one another are each hydrogen or fluorine; A is sulfonyl; Y is phenyl substituted by methyl, methoxy, fluorine, chlorine, trifluoromethyl and/or by a COOCH₃ group; R is hydrogen, methyl, trifluoromethyl, allyl or propargyl; and in which, furthermore, the group

represents

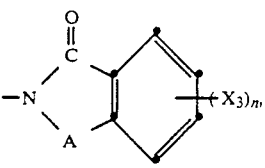

wherein A is sulfonyl; X₃ is chlorine; and n is zero or 1.

5. Compounds of formula I according to claim 1 in which $X_1$ and $X_2$ independently of one another are each hydrogen or fluorine; A is sulfonyl; Y is phenyl substituted by methyl, fluorine, chlorine and/or by trifluoromethyl; R is hydrogen, methyl, allyl or propargyl; and in which, furthermore,

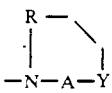

represents the group

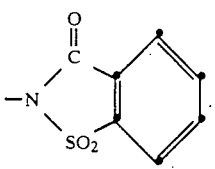

6. A compound from the group:

N-(benzo-1,2,3-thiadiazol-7-ylcarbonyl)-2-sulfobenzoic acid imide;

N-4-chlorophenylsulfonylbenzo-1,2,3-thiadiazole-7-carboxylic acid amide;

N-2-fluorophenylsulfonylbenzo-1,2,3-thiadiazole-7-carboxylic acid amide;

N-allyl-N-phenylsulfonylbenzo-1,2,3-thiadiazole-7-carboxylic acid amide;

N-phenylsulfonyl-4-fluorobenzo-1,2,3-thiadiazole-7-carboxylic acid amide;

N-4-methylphenylsulfonyl-5-fluorobenzo-1,2,3-thiadiazole-7-carboxylic acid amide;

N-phenylsulfonylbenzo-1,2,3-thiadiazole-7-carboxylic acid amide;

N-(5-fluorobenzo-1,2,3-thiadiazole-7-carbonyl)-2-sulfobenzoic acid imide.

7. A composition for protecting plants against attack by microorganisms that contains an effective amount of an active component comprising at least one compound of the formula

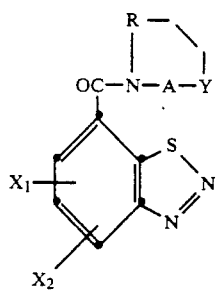
(I)

in which X₁ and X₂ independently of one another are each hydrogen or together 1 to 3 halogen atoms; A is sulfonyl or carbonyl; Y is phenyl or phenyl substituted by $C_1$–$C_2$alkyl, $C_1$–$C_2$alkoxy, halogen, $C_1$–$C_2$haloalkyl, $C_1$–$C_2$alkoxycarbonyl, $C_1$–$C_3$alkanoyloxymethyl, cyano and/or by nitro; R is hydrogen, $C_1$–$C_4$alkyl, $C_1$–$C_4$haloalkyl, $C_3$–$C_5$alkenyl or $C_3$–$C_5$alkynyl; and in which, furthermore, the group

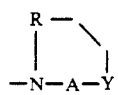

represents

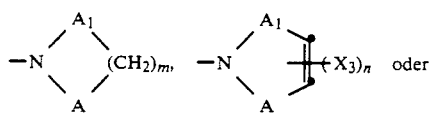

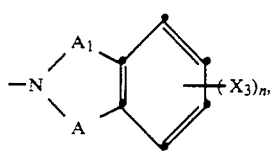

wherein A₁ is methylene, carbonyl or sulfonyl; X₃ is hydrogen, methyl or halogen; m is 2, 3 or 4; and n is zero, 1 or 2.

8. A composition of claim 18 wherein the active component comprises at least one compound in which X₁ and X₂ independently of one another are each hydrogen or together from 1 to 3 fluorine atoms; A is sulfonyl or carbonyl; Y is phenyl substituted by methyl, methoxy, halogen, trifluoromethyl, a COOCH₃ group, cyano and/or by nitro; R is hydrogen, methyl, ethyl, trifluoromethyl, allyl or propargyl; and in which, furthermore, the group

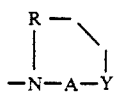

represents

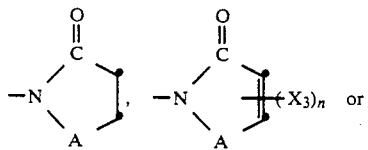

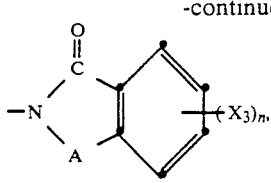

wherein A is sulfonyl or carbonyl; X₃ is methyl or halogen; and n is zero, 1 or 2.

9. A composition of claim 7 wherein the active component comprises at least one compound selected from the group consisting of
N-(benzo-1,2,3-thiadiazol-7-ylcarbonyl)-2-sulfobenzoic acid imide;
N-4-chlorophenylsulfonylbenzo-1,2,3-thiadiazole-7-carboxylic acid amide;
N-2-fluorophenylsulfonylbenzo-1,2,3-thiadiazole-7-carboxylic acid amide;
N-allyl-N-phenylsulfonylbenzo-1,2,3-thiadiazole-7-carboxylic acid amide;
N-phenylsulfonyl-4-fluorobenzo-1,2,3-thiadiazole-7-carboxylic acid amide;
N-4-methylphenylsulfonyl-5-fluorobenzo-1,2,3-thiadiazole-7-carboxylic acid amide;
N-phenylsulfonylbenzo-1,2,3-thiadiazole-7-carboxylic acid amide;
N-(5-fluorobenzo-1,2,3-thiadiazole-7-carbonyl)-2-sulfobenzoic acid imide.

10. A method of protecting plants against attack by phytopathogenic microorganisms which comprises applying to the plant or locus of the plant an effective amount of an active ingredient comprising at least one compound of the formula

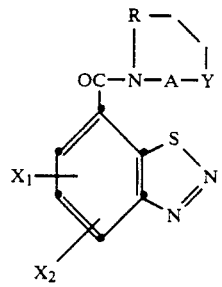
(I)

in which X₁ and X₂ independently of one another are each hydrogen or together 1 to 3 halogen atoms; A is sulfonyl or carbonyl; Y is phenyl or phenyl substituted by $C_1$–$C_2$alkyl, $C_1$–$C_2$alkoxy, halogen, $C_1$–$C_2$haloalkyl, $C_1$–$C_2$alkoxycarbonyl, $C_1$–$C_3$alkanoyloxymethyl, cyano and/or by nitro; R is hydrogen, $C_1$–$C_4$alkyl, $C_1$–$C_4$haloalkyl, $C_3$–$C_5$alkenyl or $C_3$–$C_5$alkynyl; and in which, furthermore, the group

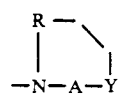

represents

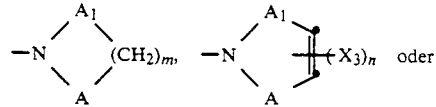

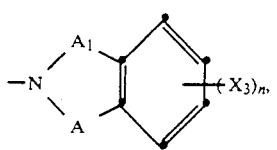

wherein $A_1$ is methylene, carbonyl or sulfonyl; $X_3$ is hydrogen, methyl or halogen; m is 2, 3 or 4; and n is zero, 1 or 2.

11. A method of claim 10 wherein the active ingredient comprises at least one compound selected from the group consisting of
N-(benzo-1,2,3-thiadiazol-7-ylcarbonyl)-2-sulfobenzoic acid imide;
N-4-chlorophenylsulfonylbenzo-1,2,3-thiadiazole-7-carboxylic acid amide;
N-2-fluorophenylsulfonylbenzo-1,2,3-thiadiazole-7-carboxylic acid amide;
N-allyl-N-phenylsulfonylbenzo-1,2,3-thiadiazole-7-carboxylic acid amide;
N-phenylsulfonyl-4-fluorobenzo-1,2,3-thiadiazole-7-carboxylic acid amide;
N-4-methylphenylsulfonyl-5-fluorobenzo-1,2,3-thiadiazole-7-carboxylic acid amide;
N-phenylsulfonylbenzo-1,2,3-thiadiazole-7-carboxylic acid amide;
N-(5-fluorobenzo-1,2,3-thiadiazole-7-carbonyl)-2-sulfobenzoic acid imide.

12. A method of claim 11 wherein the phytopathogenic microorganisms are fungal organisms and/or bacterial.

13. A method according to claim 10 wherein the phytopathogenic microorganisms are fungal organisms and/or bacteria.

* * * * *